United States Patent [19]

van der Knaap

[11] Plant 4,889

[45] Sep. 21, 1982

[54] CHRYSANTHEMUM NAMED YELLOW WESTLAND

[75] Inventor: Jacques C. M. van der Knaap, De Lier, Netherlands

[73] Assignee: Pan-American Plant Company, Parrish, Fla.

[21] Appl. No.: 193,033

[22] Filed: Oct. 2, 1980

[51] Int. Cl.[3] ..... A01H 5/00

[52] U.S. Cl. ..... Plt./78

[58] Field of Search ..... Plt./74–83

*Primary Examiner*—James R. Feyrer

*Attorney, Agent, or Firm*—Chas. W. Rummler

[57] ABSTRACT

A new and distinct chrysanthemum for glasshouse culture to produce cut flowers and pot plants, distinguished in particular, by the yellow coloration of its medium sized blooms, its vigorous and upright growth habit, and its year around flowering capability in response to photoperiod control. The title of this application is the European denomination for this variety. In the United States, this variety is marketed as "Westland Yellow".

3 Drawing Figures

BACKGROUND OF THE NEW PLANT

This new chrysanthemum cultivar originated as a sport of the variety "Westland" (U.S. Plant Pat. No. 4,589) and was produced by me by radiation breeding at De Lier, Holland, in 1977. I reproduced this plant by means of cuttings of the original plant at De Lier, Holland, and found that it retained substantially all of the characteristics of its parent, except flower color. Subsequent propagation of this new plant by cuttings and through successive generations has demonstrated that its distinctive features hold true and appear to be firmly fixed. Commercial scale propagation of this variety is now being done by cuttings at Cortez, Fla., and at West Chicago, Ill., as well as at De Lier, Holland.

DESCRIPTION OF THE DRAWINGS

This new chrysanthemum variety is illustrated by the accompanying drawings, of which sheet 1 is a full color photographic view of a potted plant in full bloom, and sheets 2 and 3 show front and back views, respectively, of typical leaves of this new plant.

DESCRIPTION OF THE NEW PLANT

The following is a detailed description of my new variety of chrysanthemum based upon observations made at West Chicago, Ill., U.S.A., in the Fall of 1979, with color designations according to the R.H.S. Colour Chart published by The Royal Horticultural Society of London, England.

THE PLANT

Origin: Sport developed by radiation breeding.
Parentage: Westland (U.S. Plant Pat. No. 4,589).
Classification:
- *Botanic.*—*Chrysanthemum morifolium.*
- *Commercial.*—Spray chrysanthemum for cut flowers.

Form: Perennial herbaceous bush.
Height: Varies between 100 to 125 cm.
Growth: Terminal; upright, strong, vigorous and strict.
Branching: None. Single cymose stem.
Foliage:
- *Quantity.*—Abundant.
- *Leaf size.*—Length — about 30 to 90 mm. Width — about 20 to 60 cm.

- *Shape.*—Ovate with cleft margin.
- *Venation.*—Pinnate.
- *Texture.*—Leathery.
- *Color.*—Upper side — 147A. Under side — 147B.
- *Petioles.*—Length: About 10 to 30 mm.

THE BUD

Size:
- *Diameter.*—About 8 to 10 mm.
- *Length.*—About 6 to 8 mm.

Form: Globular.
Opening rate: Normal.
Color:
- *When phyllaries first divide.*—8B.
- *When petals begin to unfurl.*—8B.

Phyllaries:
- *Number.*—Approximately 15.
- *Shape.*—Lanceolate.

Peduncle: Rigid, erect and strong.
- *Length.*—Varies.
- *Surface texture.*—Canescent.
- *Color.*—138A.

THE FLOWER

Blooming habit: Normally intermittent.
Recommended flowering: Year around with photoperiod control.
Blooms:
- *Flower type.*—Composite.
- *Size.*—Medium. Diameter — about 60 to 90 mm. Depth — about 12 to 20 mm.

Borne: Cymose on a strong, upright main stem.
Shape: Cup-shaped when bloom first opens, becoming flat as the bloom matures.
Petalage:
- *Phyllaries.*—Approximately 15 in number.
- *Florets.*—Many ray florets, few disc florets, all in imbricated arrangement.
- *Form.*—Quill with entire margin, open tip and rounded incised apex.

Appearance: Satiny.
Color:
- *Outer ray florets.*—Upper side — 8B. Reverse side — 8B.
- *Inner florets.*—Upper side — 8A. Under side — 8A.
- *Central florets.*—1B.

Flower stem: Strong and upright.
*Color.*—138A.
Persistence: Florets hang on and dry.
Fragrance: Typical chrysanthemum.
Lasting quality:
*On plant.*—4 weeks.
*As cut flower.*—4 weeks.

REPRODUCTIVE ORGANS

Stamens: Few in number and with syngenesious arrangement.
Pistils: Number — one for each floret.

*Styles.*—Color: Greenish-Yellow.
*Stigmas.*—Color: Greenish-Yellow.
Ovaries: Inferior bicarpellate.

This sport is substantially the same as its parent "Westland" in all of its characteristics except the yellow color which is new and distinctive in this sport.

I claim:

1. A new and distinct variety of chrysanthemum plant, substantially as herein shown and described, characterized by its yellow quill-shaped ray florets.

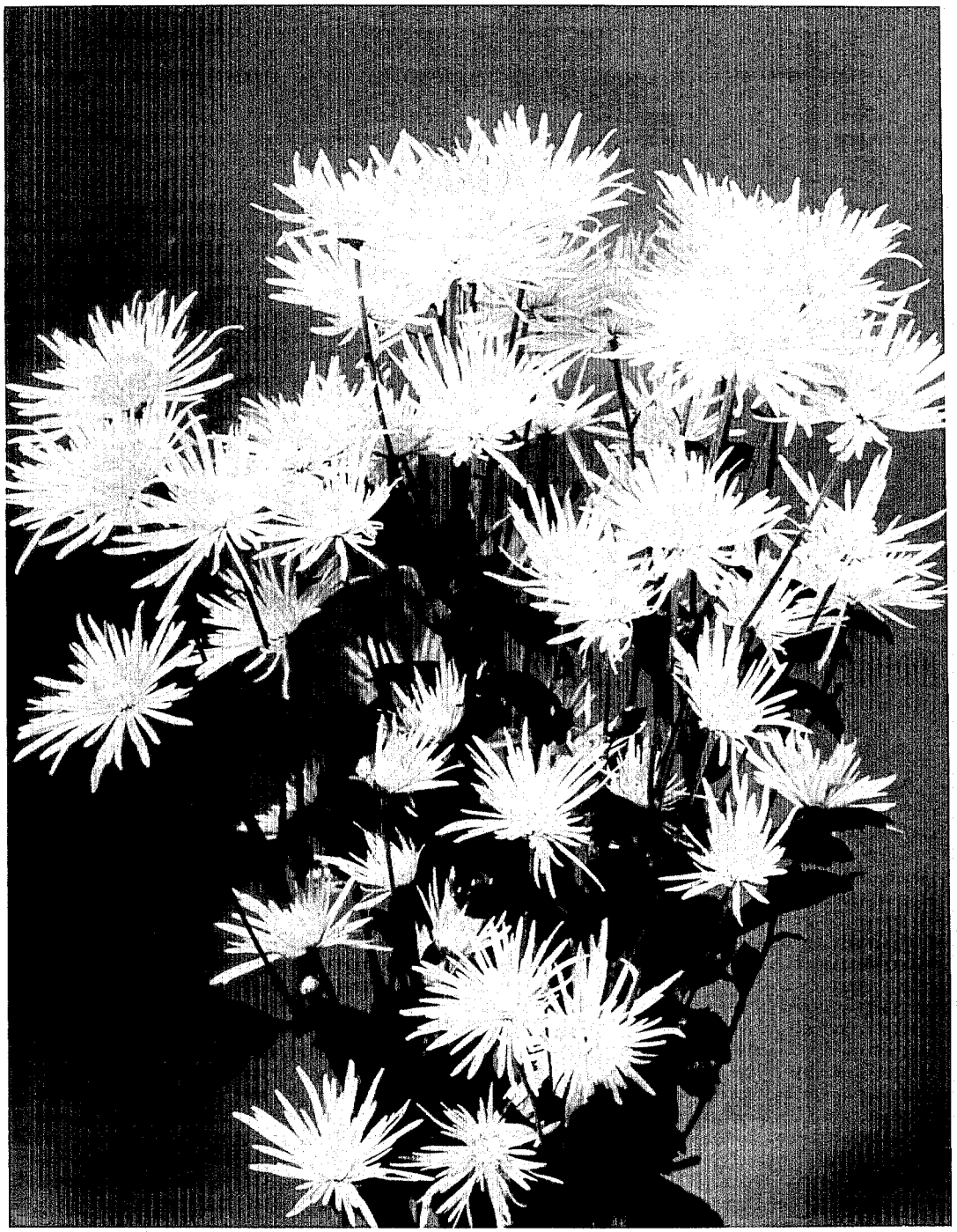

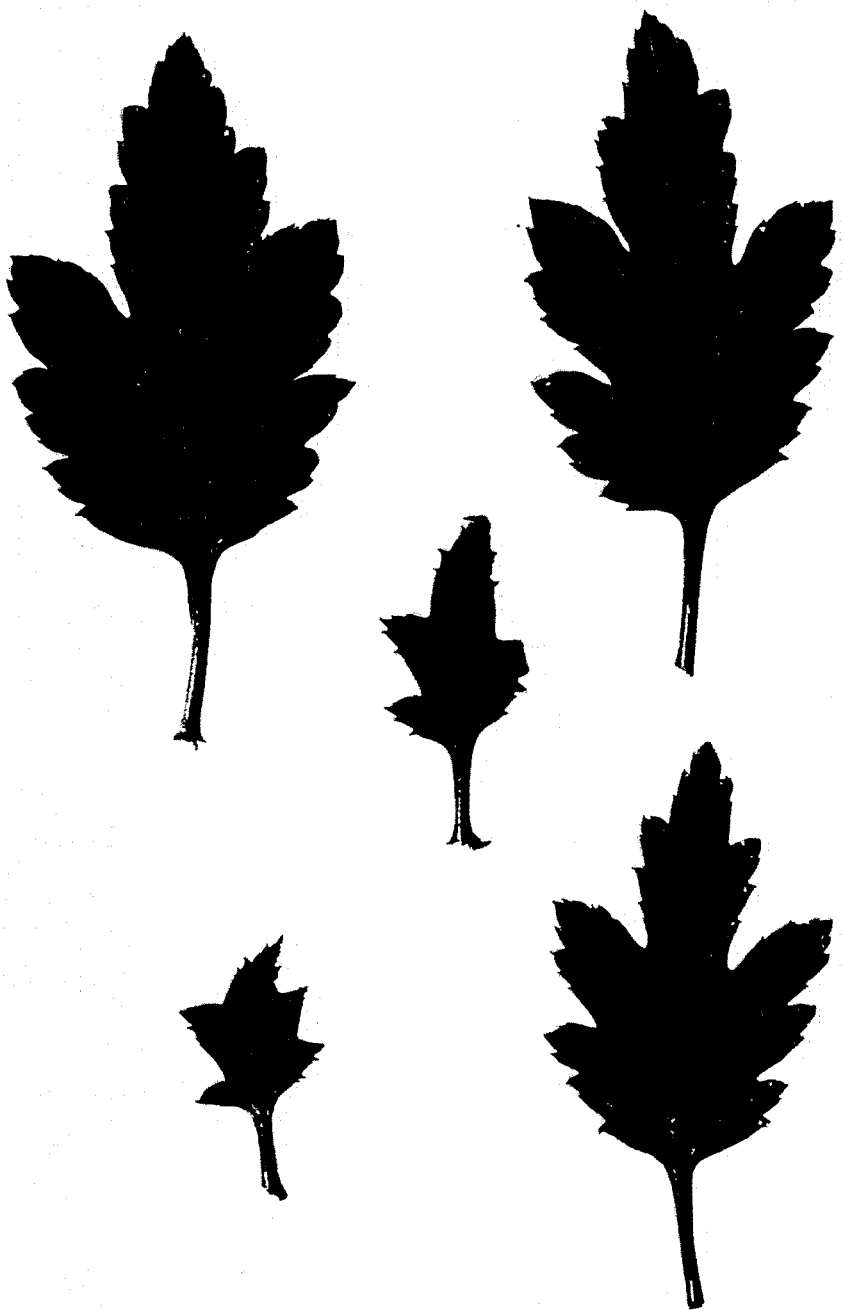

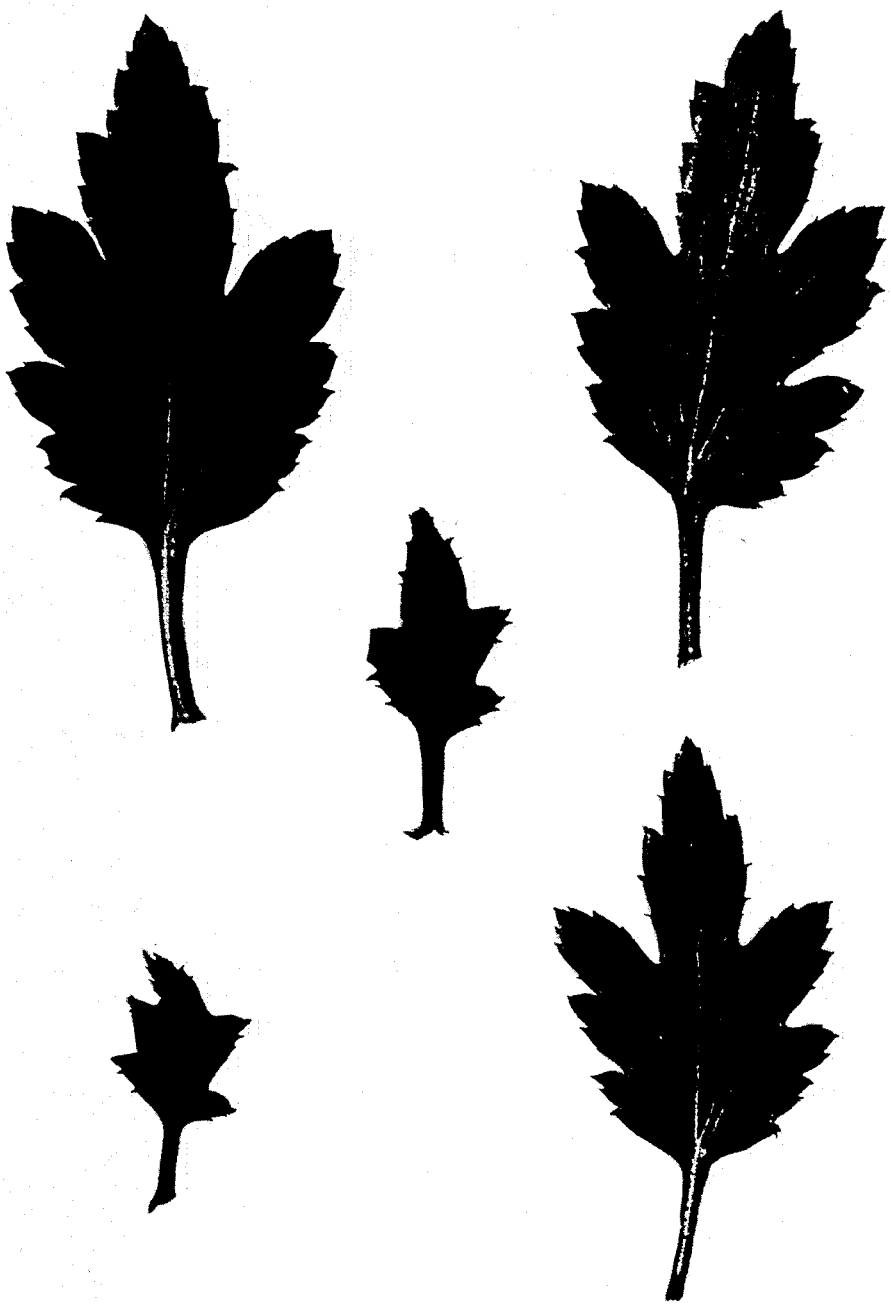

* * * * *